(12) United States Patent
Boddie et al.

(10) Patent No.: US 11,779,122 B2
(45) Date of Patent: Oct. 10, 2023

(54) ADJUSTABLE BREAST PUMP FLANGE

(71) Applicant: RESTFUL PUMP, INC., Pembroke, MA (US)

(72) Inventors: Micolene Boddie, Lakeville, MA (US); Blake Sama, Boston, MA (US)

(73) Assignee: RESTFUL PUMP, INC., Pembroke, MA (US)

( * ) Notice: Subject to any disclaimer, the term of this patent is extended or adjusted under 35 U.S.C. 154(b) by 0 days.

(21) Appl. No.: 18/054,236

(22) Filed: Nov. 10, 2022

(65) Prior Publication Data

US 2023/0072268 A1 Mar. 9, 2023

Related U.S. Application Data

(63) Continuation of application No. 16/851,673, filed on Apr. 17, 2020, now Pat. No. 11,523,688.

(51) Int. Cl.
| | |
|---|---|
| *A47C 9/00* | (2006.01) |
| *A61M 1/06* | (2006.01) |
| *A47C 9/04* | (2006.01) |
| *A47C 7/62* | (2006.01) |

(52) U.S. Cl.
CPC .............. *A47C 9/005* (2013.01); *A47C 7/622* (2018.08); *A47C 9/04* (2013.01); *A61M 1/064* (2014.02)

(58) Field of Classification Search
CPC ........ A47C 9/005; A47C 7/622; A62M 1/062; A61M 1/06; A61M 1/064; A61M 1/062
See application file for complete search history.

(56) References Cited

U.S. PATENT DOCUMENTS

| | | |
|---|---|---|
| 78,472 A | 6/1868 | Neuhaus |
| 4,552,404 A | 11/1985 | Congleton |
| 4,589,699 A | 5/1986 | Dungan |
| 4,772,262 A | 9/1988 | Grant |
| 5,149,174 A | 9/1992 | Charash |
| 5,551,583 A | 9/1996 | Sachathamakul |
| 5,667,278 A | 9/1997 | Li |
| 6,502,262 B1 | 1/2003 | Piscopo |
| 6,974,439 B1 | 12/2005 | McKendry |
| 7,070,241 B2 | 7/2006 | Saulnier et al. |
| 7,540,049 B2 | 6/2009 | Sklenarik et al. |
| 7,784,871 B2 | 8/2010 | Cochran |
| 7,819,839 B2 | 10/2010 | Gillan |
| 7,900,630 B2 | 3/2011 | Geiselhart |
| 8,043,255 B2 | 10/2011 | Weston |
| 8,052,634 B2 | 11/2011 | Thommen et al. |
| 8,142,393 B2 | 3/2012 | Myers |

(Continued)

FOREIGN PATENT DOCUMENTS

| | | | |
|---|---|---|---|
| CN | 203280090 | 11/2013 | |
| EP | 3058967 A1 * | 8/2016 | .............. A61M 1/06 |

(Continued)

*Primary Examiner* — Milton Nelson, Jr.
(74) *Attorney, Agent, or Firm* — Troutman Pepper Hamilton Sanders LLP (Rochester)

(57) ABSTRACT

An adjustable breast pumping flange is provided. The breast pumping flange allows for adjustment of the flange angle relative to a bottle to which the flange connects. This allows for a nursing mother to more comfortably position the flanges and bottles during a pumping session. This increased comfort in turn allows for improved and more efficient milk collection.

19 Claims, 9 Drawing Sheets

(56) References Cited

U.S. PATENT DOCUMENTS

| | | | |
|---|---|---|---|
| 8,579,874 B1 * | 11/2013 | Barack | A61M 1/06 604/74 |
| 8,590,968 B2 | 11/2013 | Zahir | |
| 9,480,783 B2 | 11/2016 | Johnson et al. | |
| 9,539,377 B2 | 1/2017 | Makower | |
| 2008/0167605 A1 | 7/2008 | Torvik | |
| 2009/0171270 A1 * | 7/2009 | Rohrig | A61M 1/066 604/74 |
| 2011/0251552 A1 * | 10/2011 | Brittner | A61J 9/00 604/74 |
| 2012/0260831 A1 | 10/2012 | McCarty | |
| 2014/0128806 A1 * | 5/2014 | Schlienger | A61M 1/067 604/74 |
| 2016/0220745 A1 | 8/2016 | Guthrie | |
| 2020/0222285 A1 * | 7/2020 | Zhang | A61M 39/08 |

FOREIGN PATENT DOCUMENTS

| | | |
|---|---|---|
| WO | 9622116 A1 | 7/1996 |
| WO | 2009044422 | 4/2009 |
| WO | 2014049068 A1 | 4/2014 |

\* cited by examiner

ADJUSTABLE BREAST PUMP FLANGE

This application is a continuation of U.S. patent application Ser. No. 16/851,673, filed Apr. 17, 2020, now issued as U.S. Pat. No. 11,523,688, which is incorporated herein by reference in its entirety.

BACKGROUND

Technical Field

The present disclosure relates generally to breast pumping systems. More particularly the present disclosure relates to a breast pump assembly having a breast pumping flange which connects to a nursing mother's breast. The flange can adjust in angle and/or position relative to the bottle into which the expressed milk flows. This allows a mother to lean forward in a relaxed position while using a breast pump to pump breastmilk.

Description of Related Art

Feeding infant children using breastmilk has a number of advantages from both a health, financial, and convenience perspective. In many instances, to build up a store of milk for feeding the infant, mothers will pump milk for later consumption. This advantageously allows a mother to return to work, and be away from the infant for periods of time.

However, many mothers struggle with nursing for many reasons, including providing enough milk volume to feed the growing child. This is a very common issue with various causes. Some causes of milk production shortages include stress and anxiety of caring for the infant, discomfort caused by nursing and pumping, and discomfort from the various body positions that must be maintained for extended periods of time during a pumping session. Often, during a pumping session, a woman is seated with poor posture. This can lead to sub-optimal positioning, leading to inefficient pumping, inefficient milk extraction, and reduced milk production.

Further, during pumping, it can be difficult and cumbersome to comfortably align the flange of a breast pump system to the breast of the pumping mother. The flange is fixed in position relative to the bottle. This causes further discomfort because a pumping mother must contort herself into various less-than-ideal positions and/or adjust the bottles to an unsteady position to keep the flanges in place with a good seal to ensure proper pumping.

Therefore, what is needed is a breast pumping system which can allow a mother who is pumping breastmilk to rest in a comfortable and physiologically ideal position.

SUMMARY

The subject matter of this application may involve, in some cases, interrelated products, alternative solutions to a particular problem, and/or a plurality of different uses of a single system or article.

In one aspect, an adjustable breast pumping flange assembly is provided. The assembly has a breast pumping flange connectable to a breast of a user, with a tube extending from a rear of the flange. A distal end of this tube is connectable to a bottle. An adjustment section is located along the length of the tube. This adjustment section allows for a multi-directional adjustment of the flange relative to the bottle, and is securable/lockable in an adjusted position. By securing the flange in position, it is discouraged from unintended movement relative to the end of the tube. This allows a user to set the position and then return to the breast pumping set up without needing to re-adjust, or worry about the flange coming out of position and/or losing suction mid-pump session.

In another aspect, a breast pumping bottle assembly is provided. The assembly has a bottle connected by tube to a breast pumping flange which is connectable to a breast of a user. An adjustment section is located along the length of the tube. This adjustment section allows for a directional adjustment of the flange relative to the bottle, and is securable in an adjusted position. By securing the flange in position, it is discouraged from unintended movement relative to the end of the tube.

In yet another aspect, a forward-leaning breast pumping chair is provided. The chair has a center post, a seat, and a base. The center post is angled forwardly relative to the base so that when a user sits on the seat, they are positioned to be leaning forward relative to the base and the flat ground that the base rests on. The chair further includes a breast pumping assembly. The assembly comprises a breast pumping table. The table is sized to hold a breast pump, and has a bottle positioned thereon. The bottle is connected by tube to a breast pumping flange which is connectable to a breast of a user. An adjustment section is located along the length of the tube. This adjustment section allows for a directional adjustment of the flange relative to the bottle, and is securable in an adjusted position. By securing the flange in position, it is discouraged from unintended movement relative to the end of the tube.

DETAILED DESCRIPTION

Figure 1:
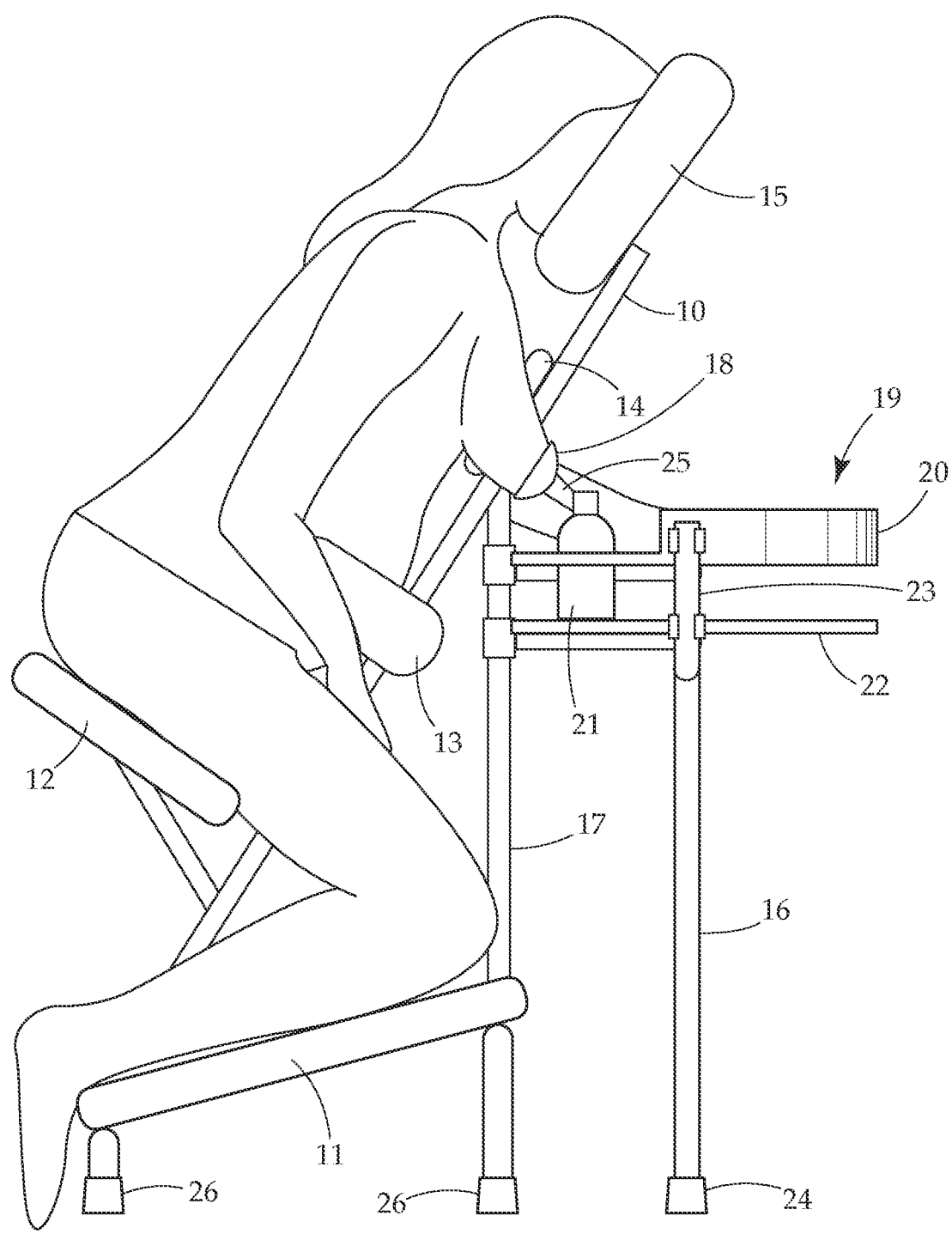
FIG. 1 provides a perspective view of an embodiment of a breast pumping chair.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

Generally, the present disclosure concerns a breast pumping flange which can be adjusted angularly. The flange (also sometimes referred to as a "shield" in the art) has a tube extending from its rear through which milk passes and which connects to a bottle, typically via a component connector but in some cases it may be directly connected to the bottle. In many embodiments, there is a valve along the flow path between the flange and component connector which allows the pump to draw negative pressure on the flange, but not within the bottle, while also allowing milk to pass through the valve on the way to the bottle. Usually the valve is a simple check valve, but other valves may be used. A component connector in turn connects to a bottle to catch and store expressed milk. The flange also connects, either directly or via the valve, to the breast pump itself which draws intermittent low pressure on the nipple of a pumping mother. The breast pumping flange is adjustable relative to at least one of the distal ends of the tube, the component connector and the bottle. This adjustability allows maximal comfort during the pumping process. Further, in many embodiments, this angular adjustment can be secured into position so that it will stay in place. In many cases, this disclosure may be particularly applicable when used in conjunction with a forward leaning breast pumping chair. For example, that disclosed in U.S. patent application Ser. No. 16/665,448 filed on Oct. 28, 2019, which is herein incorporated in its entirety by reference. Such a chair may allow the mother's front to rest on various supports in a forwardly inclined position. A breast pump table is positioned ahead of the mother's breasts, which can be connected to bottles and a breast pumping flange. The mother, once positioned on the chair, can connect the breast shields and activate the pump, allowing her to pump in an ideal position. However, as this forward leaning position may not align perfectly with traditional breast pumping flange angles, it is desirable to adjust the angle of the breast pumping flange while still allowing the bottles to rest flat on a surface. Moreover, the shape of women's breast varies, and also changes during the post-partum and nursing periods. Therefore, it is expected and almost certain that the angle of the breast pumping flange relative to the bottle will need to change. The breast pumping system disclosed utilizes gravity (by the forward-leaning) as well as optimal body positioning and comfort to allow for maximum pumping success. The adjustable flange can be particularly useful when it can be secured into a particular position, thereby keeping it in optimal position until the pumping mother adjusts it intentionally. This prevents the flange from coming out of the desired position when being manipulated as is done frequently during cleaning, repositioning, removing the bottles, moving the flange from place to place, and the like. As is well known in the art, flanges and other breast pumping components are moved, cleaned, swapped out with others, and the like up to many times per day. As such, keeping the adjusted flanges secured in an adjusted position, without having to re-position it every time, is greatly desirable.

In one embodiment, a breast pump table may be positioned on a forward leaning breast pumping chair at approximately breast-level when a user is resting on the chair. This puts the breast pump in an easily accessible position for the mother. Various structures may be employed to aid in holding the breast shields, and bottles connected thereto, to the breasts. Positional adjustment as well as angular adjustment of the flange holds the flanges properly against the breast, while the bottles can sit flat on the table/shelf or whatever they are resting/held on. This allows for hands-free operation, increasing relaxation, improved positional mechanics, and comfort. Because of the differing and variable shape, location, and size of the breasts and nipples of nursing mothers, adjustability of the flange angles and positions is necessary. Once the proper adjustment is made however, it is very advantageous to secure the flange in this adjusted position so that adjustment isn't required each pumping session. In many embodiments, in addition to the flexible flanges of this disclosure, the position and orientation of the breast holder panel with respect to the chair may be adjustable in numerous directions to optimize comfort to the user, and to adjust to the mother's changing post-partum body. Other solutions to hold the shields to the breasts may include a strap, special bra designed for such a use, securing the bottles in position, and the like. In some embodiments, the flange angle may be adjustable without a secondary securing structure and need not be securable in place.

Turning now to FIG. 1, a perspective view of an embodiment of the breast pumping system integrated into a forward-leaning chair is provided. The chair is based around a central post 10 which angles a seat 12 forward relative to a base resting on the floor. In certain embodiments the base may have feet 26 which are made to contact the floor. In other embodiments (not shown) the base may have casters, allowing easy movement of the chair along the floor. Casters may be secured and/or retracted to safely hold the chair in place when being used. A seat 12, shin rests 11, abdomen support 13, chest support 14, and head rest 15 all provide support to a person's body resting in the chair. These may each be adjustable in position and orientation in height, angle, and in some cases, lateral direction, in certain embodiments, so as to maximize comfort and relaxation to the user. The forward-leaning chair and breast pumping system can be seen in use by a user who is pumping breastmilk. Bottle 21, rests on a shelf 22 and the breast pumping flange 18 is adjustable and securable via collar 30, which allows adjustment of the direction of the flange 18 relative to bottle 21, and also allows the position of the flange 18 to be secured into positon, so it is not accidentally moved out of position. The elements of the breast pumping chair may fold relative to the central post, allowing it to be easily compacted for transport and movement.

In this view, the breast pumping components are built in to the chair, although as noted above, the components may be removably attached or positioned nearby, in other embodiments. As shown in the FIG. 1, a support bar 17 extends from the base to the central post 10. A breast pump table 19 and bottle shelf 22 are connected to this bar 17 and may be slideable along it. Other embodiments may provide only a single table 19 where both the breast pump and bottles 21 sit. In this embodiment, table 19 has a ridge 20 around at least part of its perimeter.

The breast pumping components are supported by a support 16 having a foot 24 resting on the ground. In this view, the shelf 22 and table 19 are attached to uprights 23 which in turn connect to support 16. In another embodiment, the breast pumping shelf 22 and table 19 may be supported by one or more support 16 legs having casters at their end, so that the shelf 22 and table 19 can be easily moved around a floor by the casters (not shown). In other embodiments, connection to the center post 10, whether directly or indirectly, and permanently or removably, may be sufficient to support the breast pumping components. Breast pump table 19 is designed to hold a breast pump and also in most embodiments, to provide convenient placement of breast pumping shields 25 which are connected to bottles 23. While shown permanently connected to the elements of the chair, it should be understood that in other embodiments, the breast pumping components (table 19 and others) may be removably connected to the chair, and in further embodiments may be movable relative to the chair while connected.

As assembled, the breast pumping chair and components allows for a mother to be optimally positioned to maximize pumping effectiveness by facing forward causing gravity to assist in milk expression, and to be in a very comfortable and relaxed position, reducing stress and relaxing the body leading to improved milk expression.

Adjustment of the flange relative to the bottle in a securable manner (allowing adjustment, and then securing this adjusted position to prevent unintended movement out of position) may be achieved in any manner. Generally an adjustment section is engaged with the flange, either directly or indirectly. This adjustment section allows for movement of the flange, and also typically allows for a securing or otherwise holding in place of the flange once adjusted, to prevent it from accidentally being moved out of its adjusted position. Non-limiting examples of these varied adjustment section are shown in FIGS. 2-10. The securing structure of the adjustment section may be anywhere along the length of the tube which extends from the flange to the bottle, before or after a valve, and before or after a component connector. It should be understood that the various lengths, thicknesses and other dimensions of the embodiments may vary from what is shown in the figures.

The adjustment sections contemplated in this disclosure may be removably connected or connectable to existing breast pumping components. For example, existing on-the-market breast pumping flanges may friction fit into the adjustment section, either directly or via an adapter. Similarly, existing thread adapters to connect to bottles may also friction fit to the adjustment section, either directly or via an adapter. In other embodiments, the components may be specifically designed to all fit together and/or may be permanently and/or integrally connected to each other.

The adjustment section may also operate as an extender to extend a distance from the bottle to the end of the breast pumping flange, further making it easier and more convenient to pump milk and allow the bottles to rest on a nearby surface. In a particular example, the adjustment section and related assembly may provide extension between the flange and the bottle such that operation on a forward leaning chair, such as that shown in FIG. 1 is facilitated by allowing the bottles to rest on the breast pumping table of, or adjacent to, the forward leaning chair.

Figure 2:
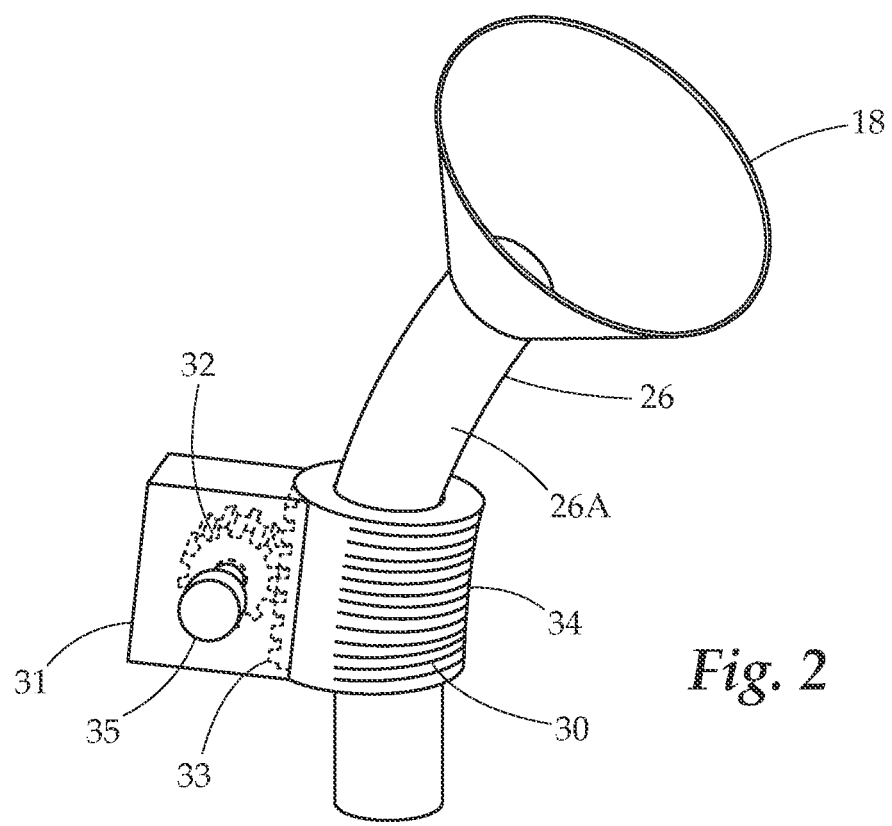
FIG. 2 provides a view of an embodiment of the adjustable breast pumping flange system.

FIG. 2 shows a view of an embodiment of the adjustable breast pumping flange system. In this view, the flange 18 connects to a flexible tube 26. This tube in turn connects to the bottle either directly or via a component connector (not shown) such as a threaded adapter. As discussed herein, the tube may be in multiple pieces or lengths, and generally refers to the flow path between the flange and the bottle. A collar 30 allows for controlled adjustment of flange 18 angle and also allows this angle to be held in place once adjusted. In this view, collar 30 is flexible via bellows 34. The tube 26A area above the collar 30 flexes as is adjusted by the change in shape of the collar 30. A housing 31 contains an adjustment section. In this embodiment, it is a knob 35 which turns a gear 32, which in turn moves teeth 33 up or down. This changes the collar 30 shape, which in turn moves tube 26A and 26, and in turn moves flange 18. Friction of the gear 32 against movement serves to lock or otherwise secure the flange 18 in place until the gear 32 is moved by the knob 35. As such, when a user is resting in the pump chair (or otherwise bumping breast milk), the bottles may be placed in position and then the flange may be adjusted to properly align with breasts and nipples of the nursing mother. This allows comfortable, relaxed, and hands-free use, all of which aid in milk expression and optimal milk capture.

Figure 3:
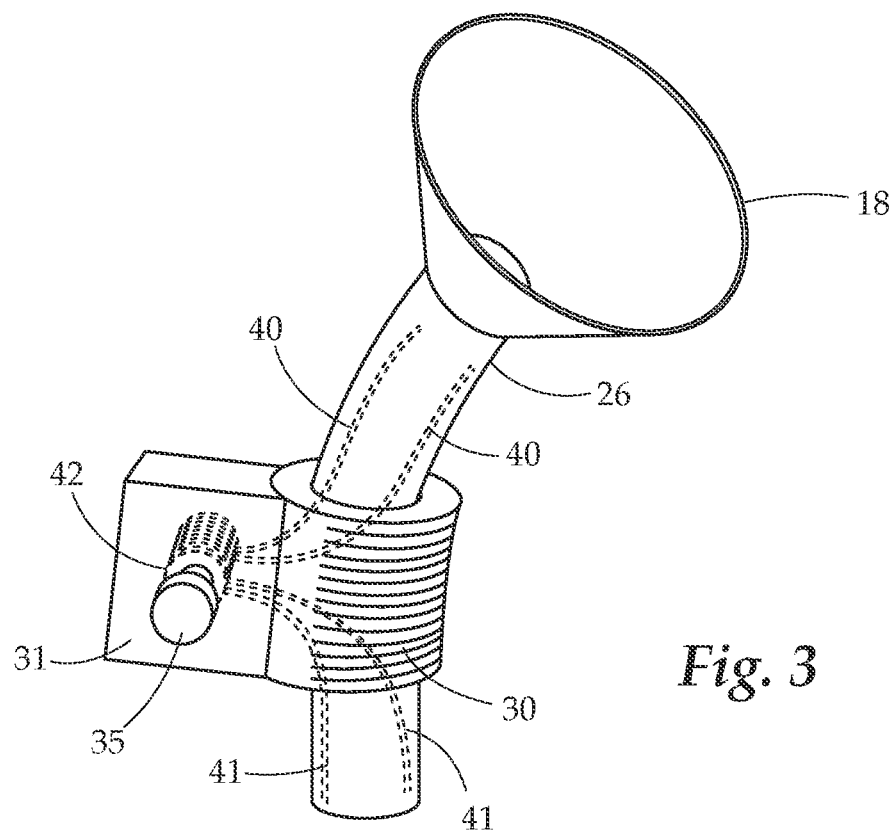
FIG. 3 provides a view of another embodiment of the adjustable breast pumping flange system.

FIG. 3 provides a view of another embodiment of the adjustable breast pumping flange system. This view is structured similarly to that of FIG. 2, however the adjustment section is different. In the housing 31, a spool 42 is adjustable by knob 35. As the spool is rotated, it tightens and loosens filaments 40 and 41. Filaments may be strings, wire, cable, and the like. The filaments 40, 41, are connected to the flexible tube 26, and upon tightening and loosening, cause the tube 26, and in turn the flange 18, to move. Friction of the spool 42 against movement serves to secure the flange 18 in place until the spool 42 is moved by the knob 35.

Figure 4:
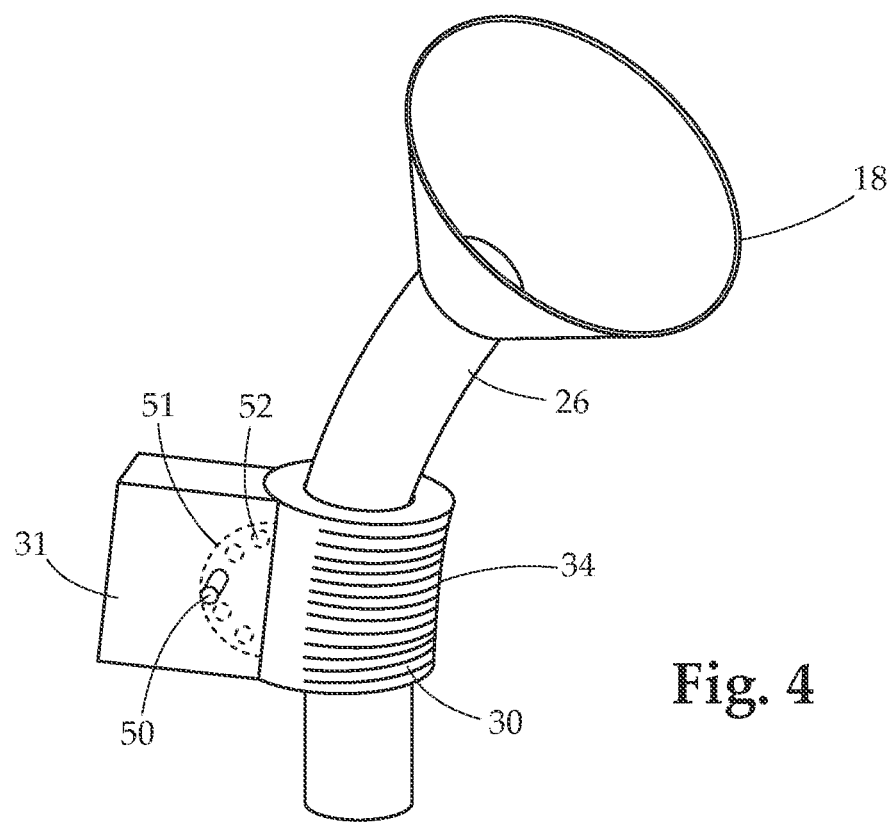
FIG. 4 provides a view of yet another embodiment of the adjustable breast pumping flange system.

FIG. 4 provides a view of yet another embodiment of the adjustable breast pumping flange system. This view is structured similarly to that of FIG. 2 with a different adjustment section. In this embodiment, the flange 18 is moved by an adjustment section within housing 31. A disc 51 having openings 52 into which peg 50 fits is used as the adjustment section. This peg 50 can be pulled out of engagement with an opening 52 and then the flange 18 may be moved manually, in turn moving the disc 51 which is connected to collar 30. Once in the desired position, peg 50 can be reinserted through a different opening, engaging the disc 51 and holding the disc 51 and in turn the flange 18 in place. In certain embodiments, the peg 50 may be prevented from being removed from the housing 31, such as by a shoulder at the end of the peg which prevents removal from a more narrow hole in the housing. In certain embodiments, the peg 50 may be spring loaded to be biased in a position passing through the disc opening 52. As in the other embodiments shown, collar 30 is flexible, as is the tube 26 passing through the collar. This allows the flange 18 angle to be adjusted, and then held in place.

Figure 5:
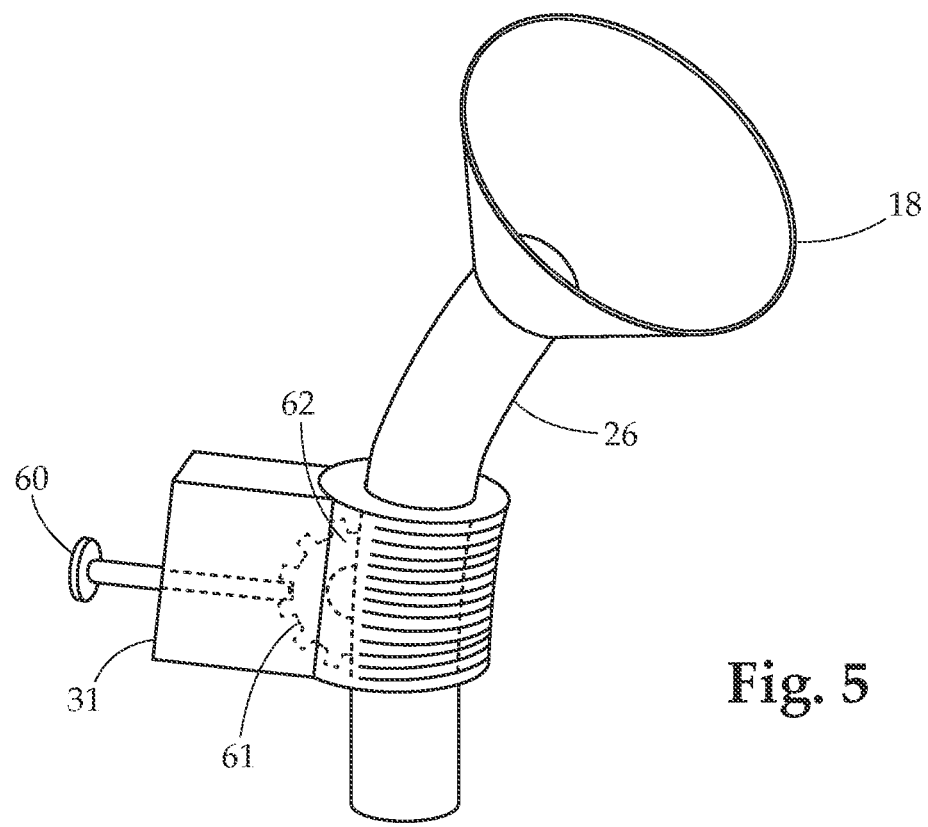
FIG. 5 provides a view of still yet another embodiment of the adjustable breast pumping flange system.

FIG. 5 provides a view of still another embodiment of the adjustable breast pumping flange system. This view is structured similarly to that of FIG. 2 with a different adjustment section. Here, a pin 60 engages with slots 61 in a gear 62. Similarly to the embodiment of FIG. 4, the pin 60 can be pulled out of engagement with a slot 61 and then the flange 18 may be moved manually, in turn moving the gear 62 which is connected to collar 30. Once in the desired position, pin 60 can be reinserted, engaging the slots 61 of the gear 62, and holding the gear 62, and in turn the flange 18, in place. In certain embodiments, the pin 60 may be prevented from being removed from the housing 31, such as by a shoulder at the end of the peg which prevents removal from a narrower hole in the housing. In certain embodiments, the pin 60 may be spring loaded to be biased in a position to engage with one of the slots 61 of the gear 62.

Figure 6A:
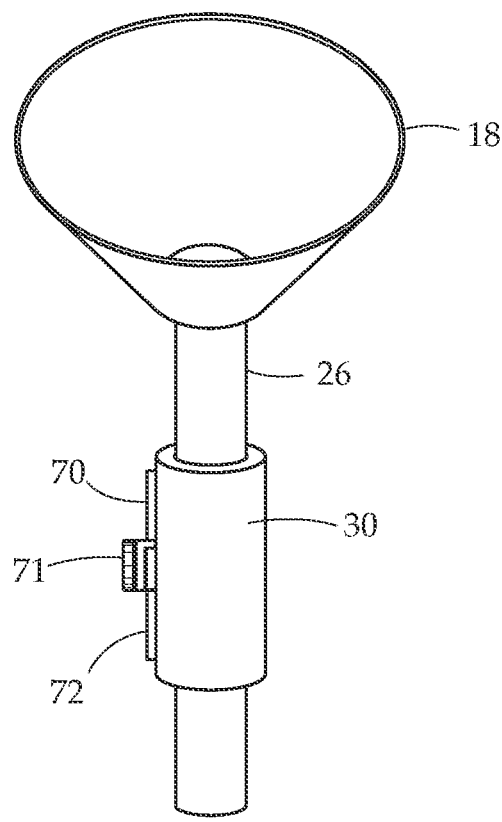
FIG. 6A provides a front view of another embodiment of the adjustable breast pumping flange system.
Figure 6B:
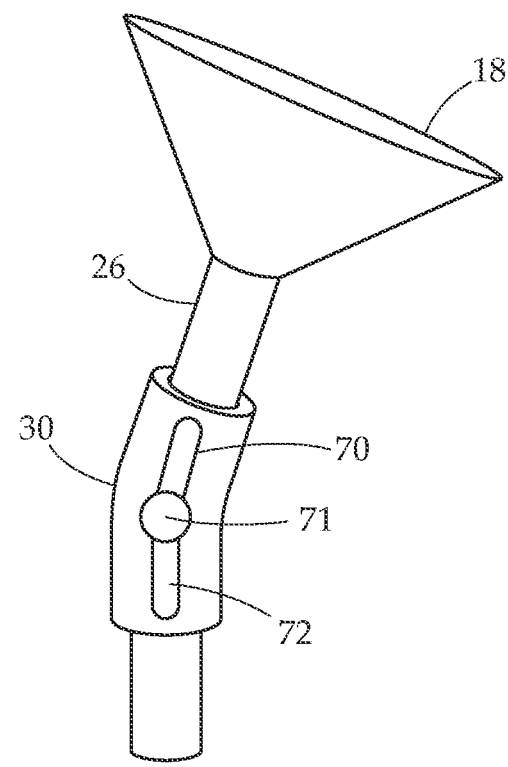
FIG. 6B provides a side view of the embodiment of the adjustable breast pumping flange system of FIG. 6A.

FIGS. 6A and 6B show front and side views of another embodiment of the adjustable breast pumping flange system. In this view, incremental angular adjustment is achieved by two arms 70, 72 which extend along at least part of the length of the collar 30. The arms are joined together at joint 71. The joint allows the arms 70, 72, to pivot relative to each other and then be secured in place. Securing in place is achieved through, for example, a frictional engagement, engaging teeth and grooves, and the like. Adjustment of the arms 70, 72 relative to each other in turn bends collar 30 and the tube 62 therein. In use, the user may release the joint by pulling, unscrewing, and so forth, and then adjust the flange 18 to the desired position, and then secure the joint in place.

Figure 7:
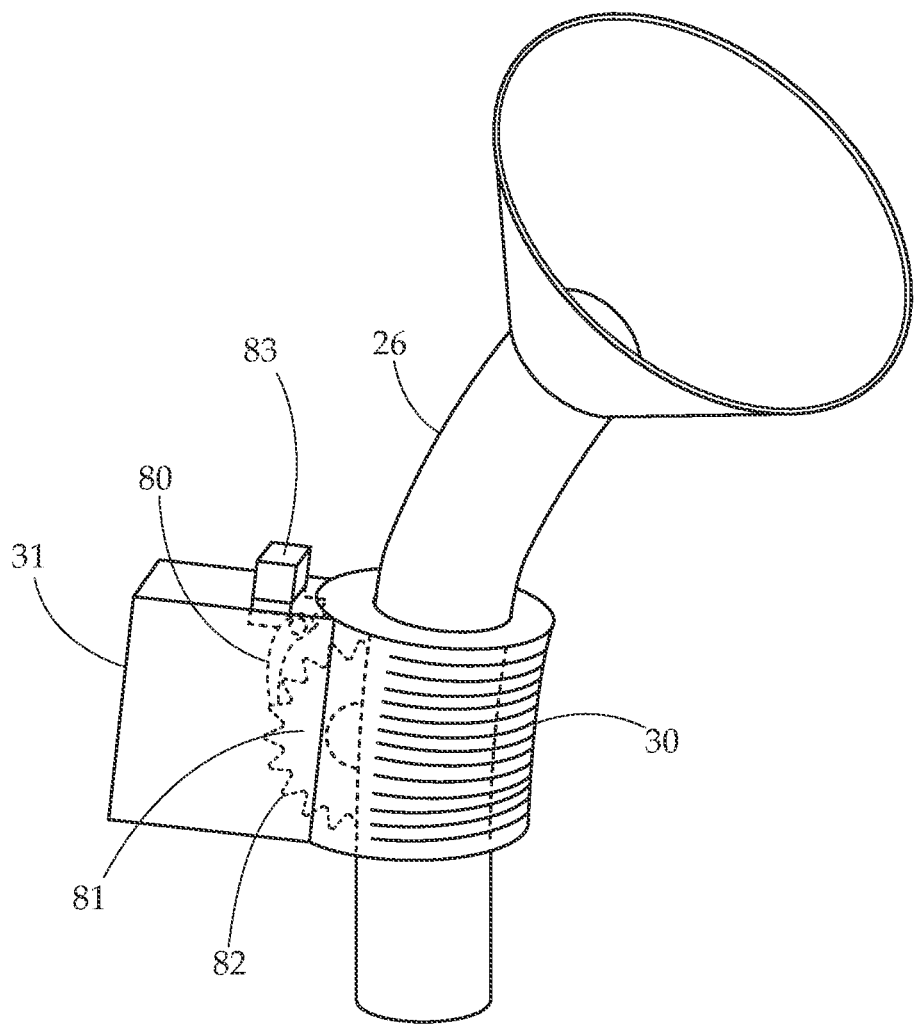
FIG. 7 provides a view of still another embodiment of the adjustable breast pumping flange system.

FIG. 7 provides a view of still another embodiment of the adjustable breast pumping flange system. This view is structured similarly to that of FIG. 2 with a different adjustment section. Here, the adjustment section within the housing 31 is a ratchet structure. The ratchet has a pawl 80 which engages with angled teeth 82. A button 83 can release the pawl from the teeth 82 to allow free movement of the flange 18. In use, a user may depress the button 83, allowing the gear 81, and in turn the flange 18 to move freely. Once in the desired position, the button 83 may be released, causing the pawl 80 to engage the teeth 82, thereby holding the collar 30, tube 26, and flange 18 in place.

Figure 8A:
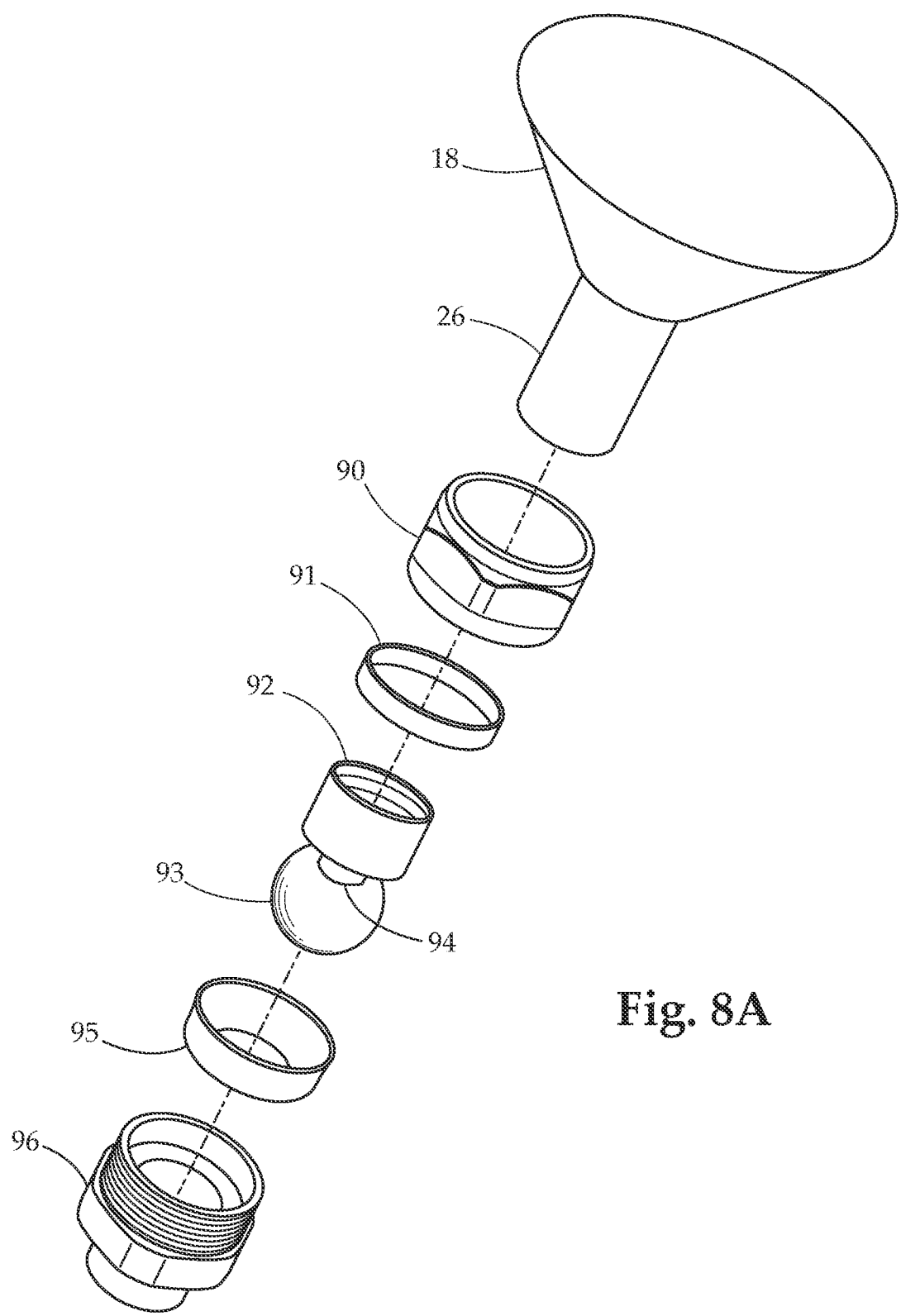
FIG. 8A provides an exploded view of another embodiment of the adjustable breast pumping flange system.
Figure 8B:
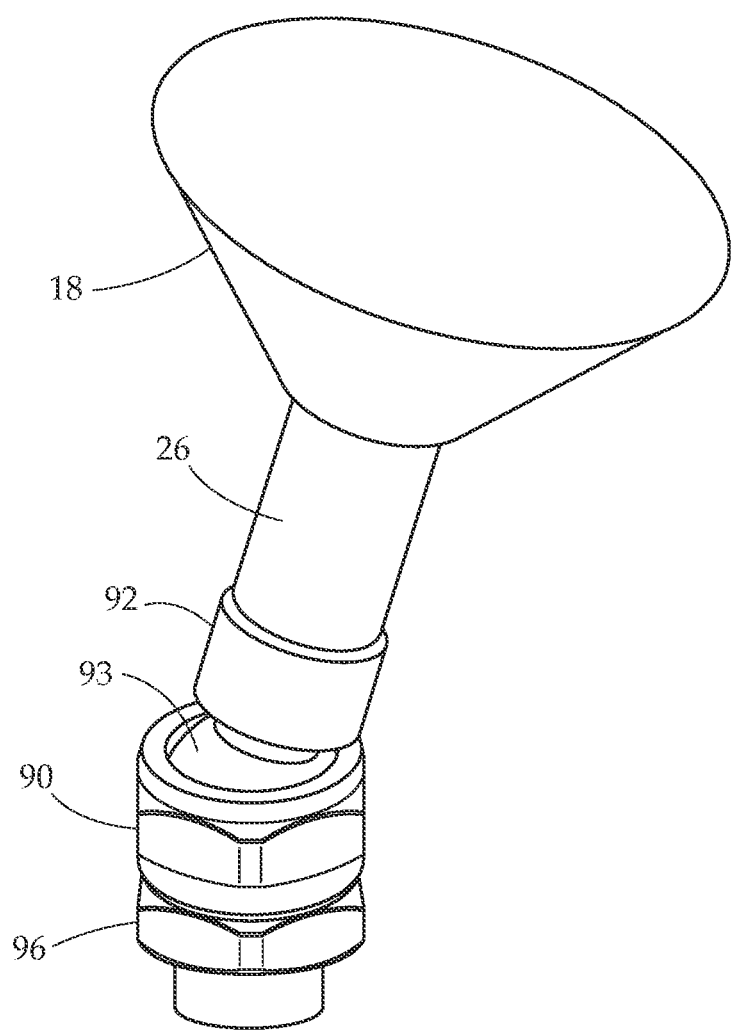
FIG. 8B provides an assembled view the embodiment of the adjustable breast pumping flange system shown in FIG. 8A.

FIGS. 8A and 8B provide another view of an embodiment of the adjustable breast pumping flange system. In this view, a flange 18 and tube 26, which may or may not be flexible, engage with a movement structure formed as ball 93 in a tube seat 92. The ball 93 has a through hole 94 allowing fluid to flow between the tube seat 92 and opposite end of the ball 92. The ball 93 is connected to a body 96 by a nut 90, washer 91, and ball seat 95. In operation, the nut 90 can be loosened, reducing frictional force on the ball 93. The ball 93 can then be moved to a desired position, which in turn moves the flange 18. Then the nut 90 can be tightened, holding the ball 93 and flange 18 in the desired position. As with all other embodiments, the opposite end of the fluid connection may directly connect or be integrally formed with a bottle, and/or may connect to the bottle via a component connector.

Figure 9:
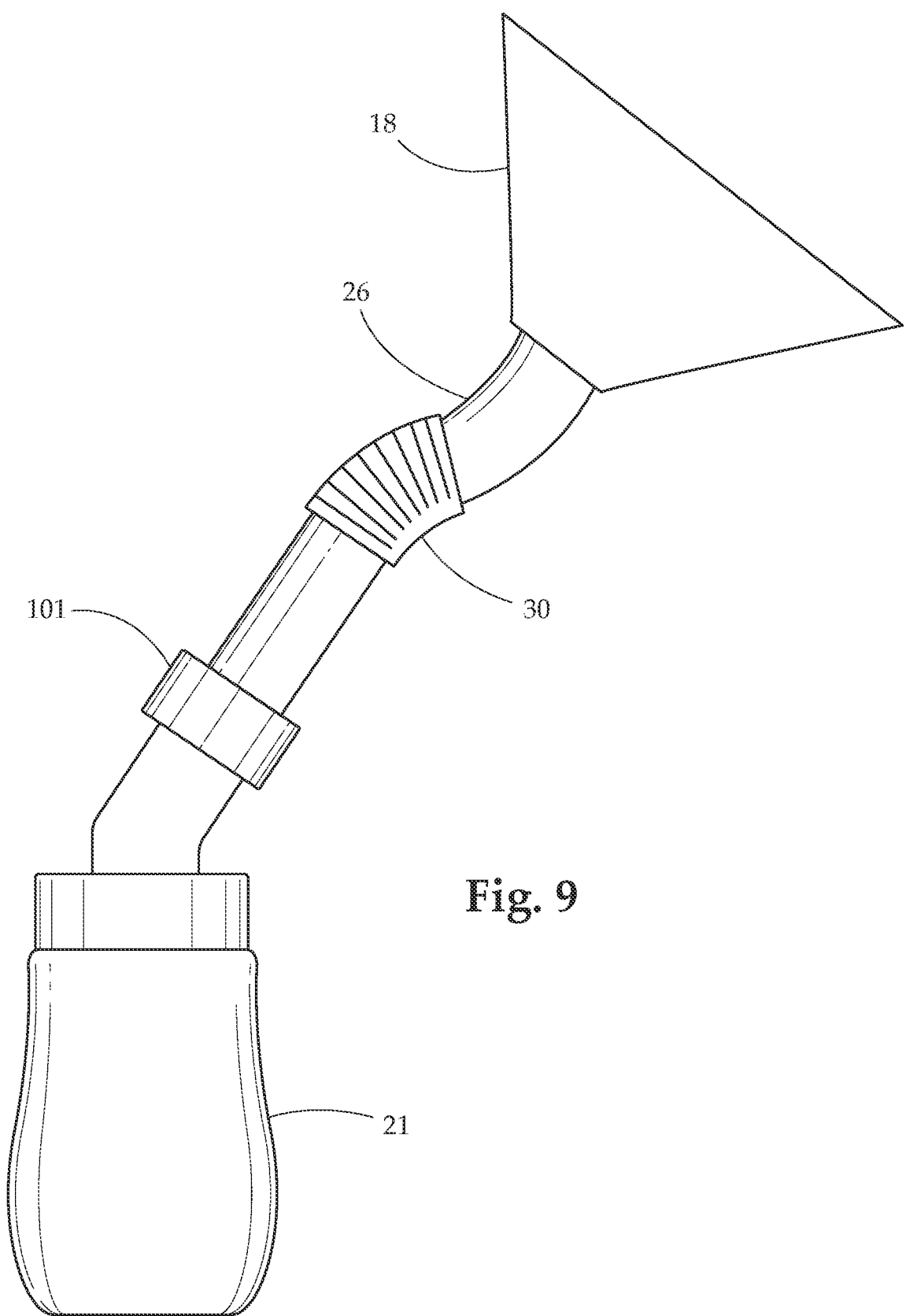
FIG. 9 provides view of the adjustable structure upstream of a valve between flange and bottle.
Figure 10:
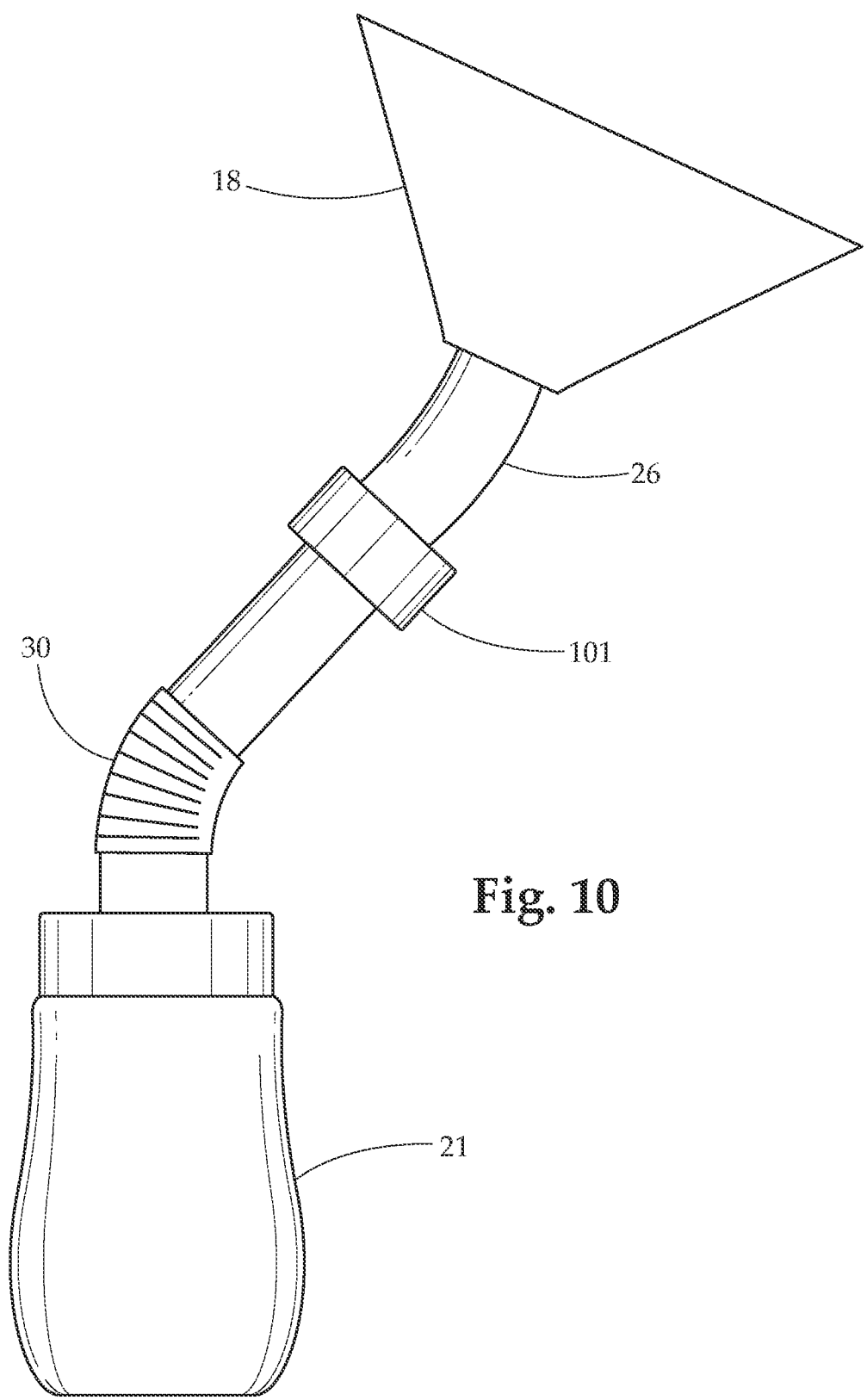
FIG. 10 provides view of the adjustable structure downstream of a valve between flange and bottle.

FIGS. 9 and 10 provide views of different embodiments having the collar upstream or downstream of the valve 101 commonly found along the flow path between bottle 21 and flange 18. In FIG. 9, the collar 30 (or any other adjustment section, including that of FIGS. 8A-8B) is positioned upstream of the valve 101, between valve 101 and flange 18. Alternatively, in FIG. 10, the collar 30 (or any other adjustment section, including that of FIGS. 8A-8B) is positioned downstream of the valve 101, between valve 101 and flange 18. In another embodiment, multiple adjustment sections may be used. These multiple adjusters may be upstream, downstream, or both upstream and downstream of the valve.

While many embodiments show the adjustment section engaging with a flexible collar, it should be understood that the same structures may be connected directly to a flexible tube, instead of the supplemental collar structure, without straying from the scope of this invention.

While several variations of the present disclosure have been illustrated by way of example in preferred or particular embodiments, it is apparent that further embodiments could be developed within the spirit and scope of the present disclosure, or the inventive concept thereof. However, it is to be expressly understood that such modifications and adaptations are within the spirit and scope of the present disclosure, and are inclusive, but not limited to the following appended claims as set forth. As noted, the forward-leaning feature of the inventive system allows for optimal breast milk expression.

What is claimed is:

1. An adjustable breast pumping flange assembly comprising:
   a breast pumping flange having a tube extending therefrom, the breast pumping flange connectable to a bottle; and
   an adjustment section allowing for a directional adjustment of the breast pumping flange relative to a distal end of the tube, the adjustment section having a locked mode in which the adjustment section is securable in an adjusted position and an unlocked mode in which the breast pumping flange is movable relative to the distal end of the tube.

2. The adjustable breast pumping flange assembly of claim 1 wherein the tube further comprises a valve along its length, the adjustment section being upstream of the valve.

3. The adjustable breast pumping flange assembly of claim 1 wherein the tube further comprises a valve along its length, the adjustment section being downstream of the valve.

4. The adjustable breast pumping flange assembly of claim 1 wherein the adjustment section further comprises a collar surrounding a portion of a length of the tube, the collar being flexible, and the portion of the length of the tube being flexible.

5. The adjustable breast pumping flange assembly of claim 4 wherein the adjustment section further comprises a housing attached to the collar, at least a portion of the adjustment section positioned within the housing, the adjustment section comprising a disc connected to the collar, the disc having a plurality of openings, a peg fitted in the housing and engageable with one of the plurality of openings, the peg movable to disengage with the one of the plurality of openings, allowing free rotation of the disc when disengaged, the free rotation of the disc allowing a movement of the breast pumping flange to adjust its position relative to the distal end of the tube.

6. The adjustable breast pumping flange assembly of claim 4 wherein the adjustment section further comprises a housing attached to the collar, at least a portion of the adjustment section positioned within the housing, the adjustment section comprising a gear connected to the collar, the gear having a plurality of slots between teeth, a pin fitted in the housing and engageable with one of the plurality of slots, the pin movable to disengage with the one of the plurality of slots allowing free rotation of the gear when disengaged, the free rotation of the gear allowing a movement of the breast pumping flange to adjust its position relative to the distal end of the tube.

7. The adjustable breast pumping flange assembly of claim 4 wherein the adjustment section further comprises two arms attached to the collar, the two arms connected at a joint, and the arms movable relative to the joint, the joint lockable to prevent a movement of the arms, such that the joint allows relative movement of the arms when in the unlocked mode, thereby allowing movement of the flange relative to the distal end of the tube, and preventing movement of the arms when in the locked mode, thereby preventing movement of the breast pumping flange relative to the distal end of the tube.

8. The adjustable breast pumping flange assembly of claim 4 wherein the adjustment section further comprises a housing attached to the collar, at least a portion of the adjustment section positioned within the housing, the adjustment section comprising a gear connected to the collar, the gear having a plurality of teeth, a ratcheting pawl positioned within the housing and engageable with one of the plurality of teeth, a button extending from the housing and operable to disengage the pawl when depressed, allowing free motion of the gear, the free rotation of the gear allowing a movement of the flange to adjust its position relative to the distal end of the tube.

9. The adjustable breast pumping flange assembly of claim 1 wherein the breast pumping flange is removably connected to the adjustment section.

10. The adjustable breast pumping flange assembly of claim 1 wherein the adjustment section comprises a ball having a through hole at least partially aligned with a lumen of the tube, the ball connected to a body such that the ball may be rotatable in angle relative to the body when in the unlocked mode, but held in place when in the locked mode.

11. A breast pumping bottle assembly comprising:
   a breast pumping flange;
   a tube extending from the breast pumping flange and configured to connect to a bottle; and
   an adjustment section allowing for a directional adjustment of the breast pumping flange relative to a distal end of the tube, the adjustment section comprising a collar surrounding or integral with at least a portion of a length of the tube, wherein the collar comprises a plurality of bellows via which the collar is flexible to facilitate the directional adjustment such that the breast pumping flange is securable in an adjusted position after the directional adjustment.

12. The breast pumping bottle assembly of claim 11 wherein the adjustment section is freely movable relative to a distal end of the tube to facilitate the directional adjustment and further comprises a locked mode via which the adjustment section is secured after the directional adjustment.

13. The breast pumping bottle assembly of claim 12 wherein the adjustment section further comprises two arms attached to the tube, the two arms connected at a joint, and the arms movable relative to the joint, the joint lockable to prevent a movement of the arms, such that the joint allows relative movement of the arms when in the unlocked mode, thereby allowing movement of the breast pumping flange relative to the distal end of the tube, and preventing movement of the arms when in the locked mode, thereby preventing movement of the breast pumping flange relative to the distal end of the tube.

14. The breast pumping bottle assembly of claim 11 wherein the adjustment section further comprises a housing attached to the collar, at least a portion of the adjustment section positioned within the housing, the adjustment section comprising a disc connected to the collar, the disc having a plurality of openings, a peg fitted in the housing and engageable with one of the plurality of openings, the peg movable to disengage with the one of the plurality of openings, allowing free rotation of the disc when disengaged, the free rotation of the disc allowing a movement of the breast pumping flange to adjust its position relative to the distal end of the tube.

15. The breast pumping bottle assembly of claim 11 wherein the portion of the tube passes through the collar and is flexible.

16. An adjustable breast pumping flange assembly comprising:
   a breast pumping flange;
   a tube extending from the breast pumping flange and connectable to a bottle; and
   an adjustment section allowing for a directional adjustment of the breast pumping flange relative to a distal end of the tube, the adjustment section comprising one or more filaments disposed proximate at least a flexible portion of the tube, the filaments configured to be adjusted to thereby adjust the flexible portion and cause the directional adjustment such that the breast pumping flange is securable in an adjusted position after the directional adjustment.

17. The adjustable breast pumping flange assembly of claim 16 wherein:
   the adjustment section allows for the directional adjustment of the breast pumping flange relative to the distal end of the tube by a rotation of a knob in communication with the tube, a rotation of the knob causing a movement of the breast pumping flange relative to the distal end of the tube in one or more directions; and
   the adjustment section further comprises a collar surrounding a portion of a length of the tube, the collar being flexible, and the portion of the tube passing through the collar being flexible.

18. The adjustable breast pumping flange assembly of claim 16 wherein the breast pumping flange or a portion of the tube is removably connected to the adjustment section.

19. The adjustable breast pumping flange assembly of claim 17 wherein the adjustment section further comprises a housing attached to the collar, at least a portion of the adjustment section positioned within the housing, the adjustment section comprising a spool rotatable by the knob extending out from the housing, at least one of the filaments rotated about the spool, a rotation of the spool by the knob pulling on the at least one of the filaments and causing the tube to move and in turn causing the breast pumping flange to move.

* * * * *